(12) United States Patent
Choi et al.

(10) Patent No.: US 8,362,267 B2
(45) Date of Patent: *Jan. 29, 2013

(54) BENZOPHENONE THIAZOLE DERIVATIVES USEFUL FOR INHIBITING FORMATION OF MICROTUBULE AND METHOD FOR PRODUCING THE SAME

(75) Inventors: Nam-Song Choi, Cheonan-si (KR); Young-Hoon Kim, Cheonan-si (KR); Jae-Kwang Lee, Cheonan-si (KR); Hee-Ryong Kang, Cheonan-si (KR); Ho-Jin Choi, Cheonan-si (KR); Seung-Kee Moon, Cheonan-si (KR); Soo-Jin Kim, Cheonan-si (KR); Gyu-Tae Park, Cheonan-si (KR); Byeong-Hoon Han, Cheonan-si (KR); Dal-Hyun Kim, Cheonan-si (KR); Jae-Hoon Choi, Cheonan-si (KR); Sung-Sook Lee, Cheonan-si (KR); Soon-Kil Ahn, Cheonan-si (KR); Kyung-Joo Lee, Cheonan-si (KR); Su-Yeal Bae, Cheonan-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 65 days.

This patent is subject to a terminal disclaimer.

(21) Appl. No.: 12/934,521

(22) PCT Filed: Mar. 5, 2009

(86) PCT No.: PCT/KR2009/001095
§ 371 (c)(1),
(2), (4) Date: Sep. 24, 2010

(87) PCT Pub. No.: WO2009/119980
PCT Pub. Date: Oct. 1, 2009

(65) Prior Publication Data
US 2011/0021582 A1 Jan. 27, 2011

(30) Foreign Application Priority Data
Mar. 26, 2008 (KR) .................. 10-2008-0027820

(51) Int. Cl.
*C07D 277/38* (2006.01)
*C07D 277/40* (2006.01)
*C07D 277/44* (2006.01)
*A61K 31/427* (2006.01)

(52) U.S. Cl. ........ 548/195; 548/190; 548/196; 514/370; 514/371

(58) Field of Classification Search .................. None
See application file for complete search history.

(56) References Cited

U.S. PATENT DOCUMENTS
8,053,439 B2 * 11/2011 Choi et al. .................. 514/256

FOREIGN PATENT DOCUMENTS
| WO | 2004/078144 A2 | 9/2004 |
| WO | 2005/009940 A1 | 2/2005 |
| WO | 2006/063585 A1 | 6/2006 |
| WO | 2008/038955 A | 4/2008 |

OTHER PUBLICATIONS

Nam, et al., "Water soluble prodrugs of the antitumor agent 3-[(3-amino-4-nriethoxyl)phenyl]-2-(3,4,5-trimethoxyphenyl) cyclopent-2-ene-1-one", Biorganic & Medicinal Chemistry, 11, 2003, pp. 1021-1029.
Braslau, et al., Synthesis of N-hydroxy peptides: Chemical ligation of O-acyl hydroxamic acids:, Organic Letters, vol. 2(2), 2000, pp. 1399-1401.
Oku, et al., "((9-fluorenylmethyl)oxy)carbonyl (fmoc) amino acid chlorides. Synthesis, characterization, and application to the rapid synthesis of short peptide segments", J. Org. Chem., 51, 1986, pp. 3732-3734.
Clemence, et al., "4-hydroxy-3-quinolinecarboxamides with antiarthritic and analgesic activities", J. Med. Chem., 31, 1988, pp. 1453-1462.
Yu, et al., "New synthesis of vaulted biaryl ligands via the snieckus phenol synthesis", Organic Letters, vol. 7(3), 2005, pp. 367-369.

* cited by examiner

*Primary Examiner* — Kamal Saeed
*Assistant Examiner* — Nyeemah A Grazier
(74) *Attorney, Agent, or Firm* — Lucas & Mercanti, LLP

(57) ABSTRACT

Disclosed are a novel thiazole-containing benzophenone derivative represented by formula 1, and an isomer thereof, a pharmaceutically acceptable salt thereof, a hydrate thereof and a solvate thereof, a pharmaceutical composition comprising the derivative, a use of the derivative as therapeutic agent and a method for preparing the derivative. The benzophenone thiazole derivatives inhibit formation of microtubules and eliminate actively proliferating cells of malignant tumors to control general cell proliferation. In formula 1, R, $R_1$ and $R_2$ are defined as above.

6 Claims, 3 Drawing Sheets

BENZOPHENONE THIAZOLE DERIVATIVES USEFUL FOR INHIBITING FORMATION OF MICROTUBULE AND METHOD FOR PRODUCING THE SAME

CROSS-REFERENCE TO RELATED APPLICATIONS

This application is a 371 of PCT/KR2009/001095 filed on Mar. 5, 2009, which claims the benefit of Korean Patent Application No. 10-2008-0027820 filed on Mar. 26, 2008, the contents of each of which are incorporated herein by reference.

TECHNICAL FIELD

The present invention relates to a thiazole-containing benzophenone derivative useful for inhibiting formation of microtubule, or an isomer thereof, a pharmaceutically acceptable salt thereof, a hydrate thereof or a solvate thereof, a pharmaceutical composition comprising the derivative, a use of the derivative as a therapeutic agent and a method for preparing the derivative. The benzophenone thiazole derivatives of the present invention inhibit formation of microtubules, eliminate actively proliferating cells of malignant tumors and thus control general cell proliferation.

BACKGROUND ART

The applicants of the present invention disclose novel benzophenone derivatives having inhibitory activity upon microtubule formation in Korean Patent No. 10-2006-0094019 (filed on Sep. 27, 2006), Korean Patent No. 10-2007-0083856 (filed on Aug. 21, 2007) claiming the benefit thereof and PCT Application No. PCT/KR2007/004625 (filed on Sep. 21, 2007).

Among the compounds disclosed in PCT/KR2007/004625, 516[{4-(2-aminothiazol-4-yl)-2-(1H-1,2,4-triazol-1-yl)phenyl}(3,4,5-trimethoxyphenyl)methanone] is found to exhibit potent mitosis inhibitory activity and cytotoxicity. From animal test results, it can be confirmed that the toxicity is caused by deposition on organs due to its low solubility.

Accordingly, the inventors of the present invention attempted to develop compounds which exhibit more efficacious pharmaceutical effects and low toxicity via improvement in solubility of benzophenone derivatives, resulting in the present invention. That is, the present invention provides novel benzophenone thiazole compounds, as derivatives of 516[{4-(2-aminothiazol-4-yl)-2-(1H-1,2,4-triazol-1-yl)phenyl}(3,4,5-trimethoxyphenyl)methanone], having efficient mitosis inhibition, superior antitumor activity, and improved solubility and thus considerably decreased toxicity.

DISCLOSURE

Technical Problem

Therefore, the present invention has been made in view of the above problems, and it is one object of the present invention to provide a compound which is toxic to directly or indirectly active mitotic cells and is useful for treating malignant tumors, viral and bacterial infection, recurrent vascular occlusion, inflammatory diseases, autoimmune diseases and psoriasis.

Accordingly, the present invention provides a novel benzophenone thiazole derivative useful for inhibiting formation of microtubules, or an isomer thereof, a pharmaceutically acceptable salt thereof, a hydrate thereof or a solvate thereof.

It is another object of the present invention to provide a pharmaceutical composition, as an active ingredient, comprising a benzophenone derivative containing thiazole useful for inhibiting formation of microtubules, or an isomer thereof, a pharmaceutically acceptable salt thereof, a hydrate thereof or a solvate thereof.

It is yet another object of the present invention to provide a method for preparing a benzophenone derivative containing thiazole useful for inhibiting formation of microtubules, or an isomer thereof, a pharmaceutically acceptable salt thereof, a hydrate thereof or a solvate thereof.

Technical Solution

In accordance with the present invention, the above and other objects can be accomplished by the provision of a compound represented by formula 1 or an isomer thereof, a pharmaceutically acceptable salt thereof, a hydrate thereof or a solvate thereof.

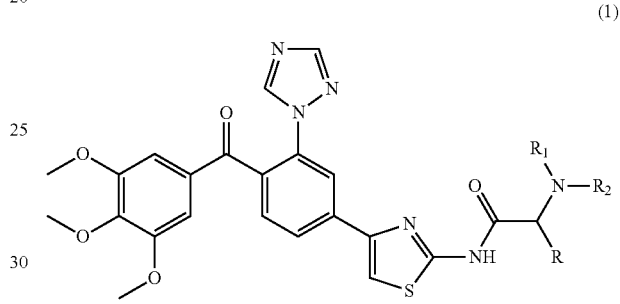

(1)

wherein $R_1$ and $R_2$ are each independently hydrogen (H) or methyl ($CH_3$); and R is hydrogen, methyl, ethyl, or one selected from compounds represented by the following moieties, in which $R_1$ and $R_2$ are joined together to form a ring:

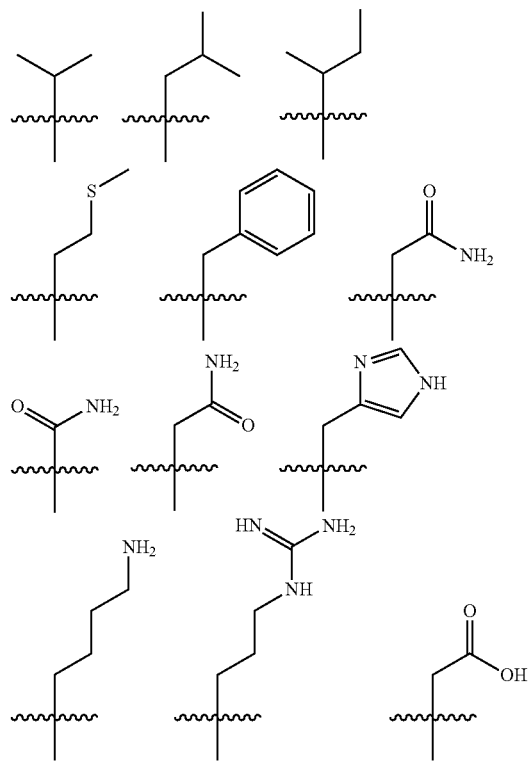

3
-continued
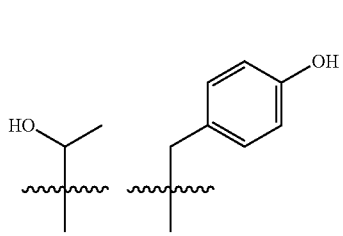
4
-continued
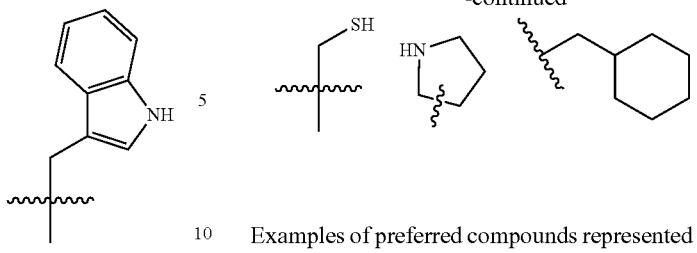
Examples of preferred compounds represented by formula 1 are shown in Table 1 below:
TABLE 1
| Compound 615 | 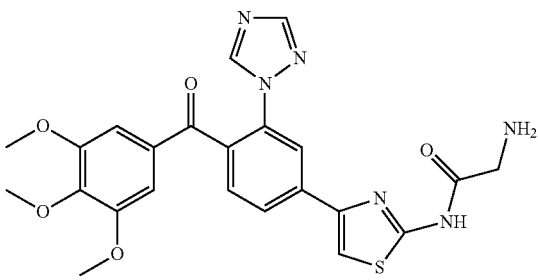 [SMILES: COc1cc(C(=O)c2ccc(-c3csc(NC(=O)CN)n3)cc2-n2cncn2)cc(OC)c1OC] |
| --- | --- |
| Compound 624 | 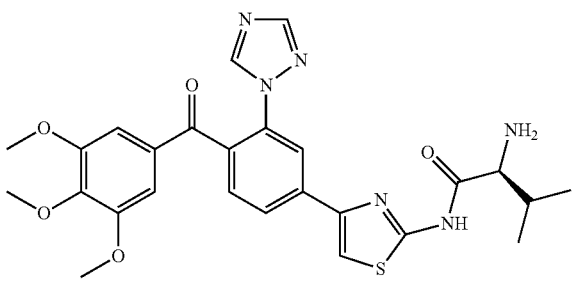 [SMILES: COc1cc(C(=O)c2ccc(-c3csc(NC(=O)[C@@H](N)C(C)C)n3)cc2-n2cncn2)cc(OC)c1OC] |
| Compound 625 | 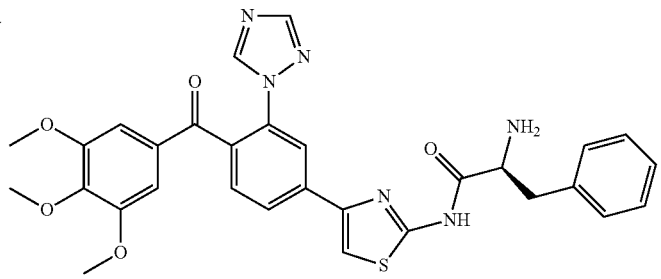 |
| Compound 631 | 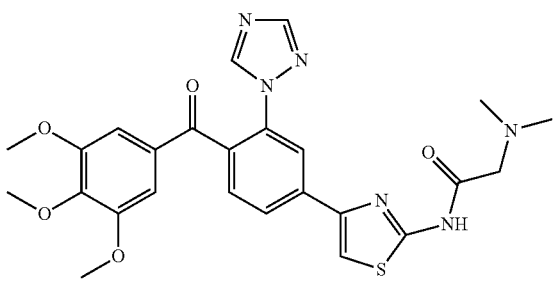 |

TABLE 1-continued

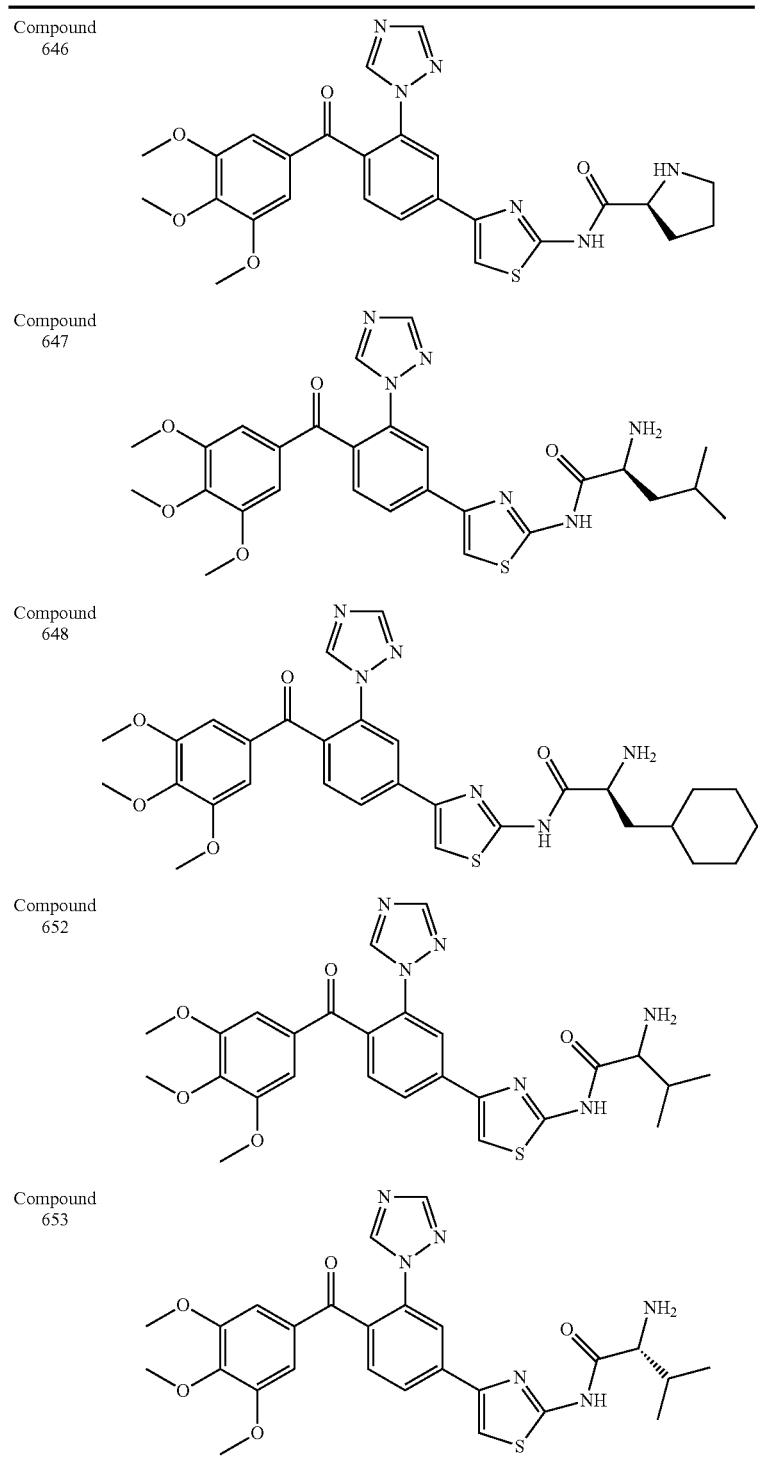

In accordance with another aspect of the present invention, provided is a pharmaceutical composition for inhibiting formation of microtubules, comprising the compound of formula 1 or an isomer thereof, a pharmaceutically acceptable salt thereof, a hydrate thereof or a solvate thereof as an active ingredient, and a pharmaceutically acceptable excipient or carrier.

Hereinafter, the method for preparing the compound will be illustrated in detail.

The compound of formula 1 may be prepared in accordance with a method disclosed in a variety of documents (Nguyen-Hai Nam et al., *Bioorg. Med. Chem.* 2003, 11, 1021; Rebecca Braslau et al., *Org. Lett.* 2000, 10, 1399; Akira Oku et al., *J. Org. Chem.* 1986, 19, 3732; Francois Clemence et al., *J. Med. Chem.* 1988, 7, 1453; Yu Su et al., *Org. Lett.* 2005, 7, 367). The preparation method of the compound of formula 1 will be illustrated in detail with reference to the following Reaction Scheme I:

[Reaction Scheme I]

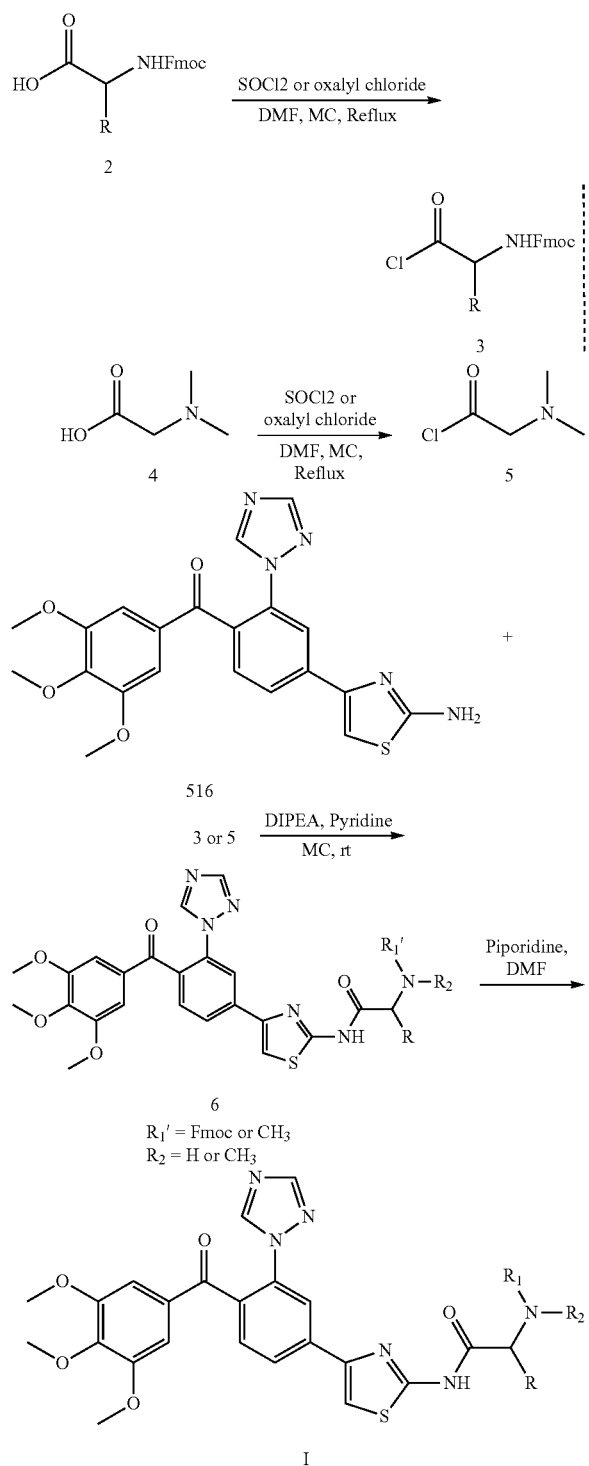

In Reaction Scheme I, Fmoc is an N-a-9-fluorenylmethoxycarbonyl group, DIPEA is diisopropylethylamine, MC is methylene chloride, ph is phenyl, DMF is N,N-dimethylformamide, and R, $R_1$ and $R_2$ are defined as above.

In accordance with Reaction Scheme I, thionyl chloride ($SOCl_2$) or oxalyl chloride is added to a compound of formula 2 or a compound of formula 4 as a starting material, respectively, to prepare a compound of formula 3 or a compound of formula 5, the compound of formula 3 or 5 reacts with a compound 516[{4-(2-aminothiazol-4-yl)-2-(1H-1,2,4-triazol-1-yl)phenyl}(3,4,5-trimethoxyphenyl)methanone] to prepare a compound of formula 6, and de-protection reaction is performed.

BRIEF DESCRIPTION OF THE DRAWINGS

The above and other objects, features and other advantages of the present invention will be more clearly understood from the following detailed description taken in conjunction with the accompanying drawings, in which.

BEST MODE

Figure 1:
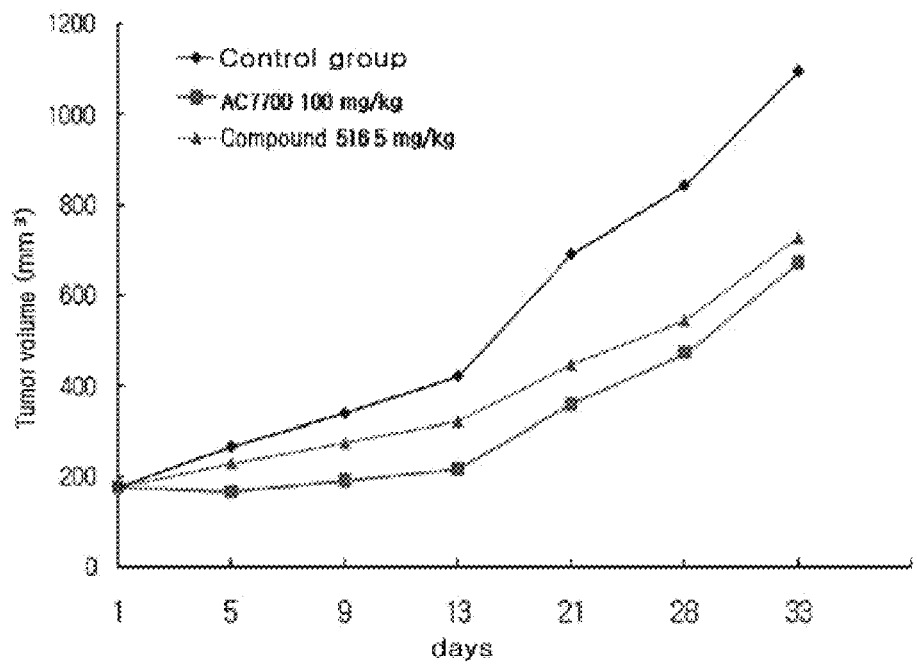
FIG. 1 is a graph showing tumor volume on each administration day of compound 516, as a result of pharmaceutical effect tests of the compound 516 using a human-derived colorectal cancer cell line (CX-1)

Now, the present invention will be described in more detail with reference to the following examples, preparation examples and experimental examples. These examples are provided only to illustrate the present invention and should not be construed as limiting the scope and spirit of the present invention.

Example 1

Synthesis of Compound 615

Synthesis of N-(4-(3-(1H-1,2,4-triazol-1-yl)-4-(3,4,5-trimethoxybenzoyl)phenyl) thiazol-2-yl)-2-aminoacetamide Fmoc-glycine (0.94 g, 3.16 mmol) and N,N-dimethylformamide (one drop) were dissolved in methylene chloride (5 mL), thionyl chloride ($SOCl_2$, 0.3 mL) was added thereto at ambient temperature and the resulting mixture was stirred under reflux for one hour. After the reaction was completed, the reaction solution was cooled to ambient temperature and was dried under reduced pressure to remove the solvent, the resulting compound (1 g) was added to a solution of the compound 516 (0.45 g, 1.07 mmol) in methylene chloride (10 mL) and pyridine (0.13 mL) and the resulting mixture was stirred at ambient temperature overnight. After the reaction was completed, the resulting product was dried under reduced pressure to remove the solvent and purified by column chromatography (SiO$_2$; MC/MeOH 40/1-10/1) to obtain a solid compound (0.54 g, 71.6%). The resulting compound (0.46 g, 0.64 mmol) was dissolved in N,N-dimethylformamide (3 mL), piperidine (76 µL) was added thereto at ambient temperature and the resulting mixture was stirred at ambient temperature for 2 hours. After the reaction was completed, the resulting solution was dried under reduced pressure to remove the solvent and the resulting product was purified by column chromatography (SiO$_2$; MC/MeOH 20/1-5/1) to obtain a white solid compound 615 (246.6 mg, 77.9%).

$^1$H NMR (400 MHz, acetone) δ 8.790 (s, 1H), 8.372 (d, J=1.48 Hz, 1H), 8.315 (dd, J=8.0, 1.6 Hz, 1H), 7.969 (s, 1H), 7.893 (s, 1H), 7.775 (d, J=8.12 Hz, 1H), 3.829-3.815 (s, 9H), 3.711 (s, 2H). (MS (ESI) m/z 495 (M$^+$+H).

Example 2

Synthesis of Compound 624 (S)—N-(4-(3-(1H-1,2,4-triazol-1-yl)-4-(3,4,5-trimethoxybenzoyl)phenyl)thiazol-2-yl)-2-amino-3-methylbutanamide A white solid compound 624 (2.25 g, 53.2%) was obtained in the same manner as in the synthesis of the compound 615.

$^1$H NMR (400 MHz, CDCl$_3$) δ 8.338 (s, 1H), 8.172 (d, J=1.52 Hz, 1H), 8.035 (dd, J=8.08, 1.40 Hz, 1H), 7.937 (s, 1H), 7.653 (d, J=8.08 Hz, 1H), 7.381 (s, 1H), 6.985 (s, 2H), 3.819 (s, 6H), 3.556 (d, J=3.6 Hz, 1H), 2.481 (m, 1H), 1.092 (d, J=6.96 Hz, 3H), 0.909 (d, J=6.92 Hz, 3H). MS (ESI) m/z 537 (M$^+$+H).

Example 3

Synthesis of Compound 625

Synthesis of (S)—N-(4-(3-(1H-1,2,4-triazol-1-yl)-4-(3,4,5-trimethoxybenzoyl)phenyl)thiazol-2-O-2-amino-3-phenylpropanamide A white solid compound 625 (13.6 mg, 21.2%) was obtained in the same manner as in the synthesis of the compound 615.

$^1$H NMR (400 MHz, CDCl$_3$) δ 8.333 (s, 1H), 8.165 (d, J=1.52 Hz, 1H), 7.935 (dd, J=8.04, 1.52 Hz, 1H), 7.654 (d, J=8.04 Hz, 1H), 7.405-7.245 (m, 6H), 6.985 (s, 2H), 3.903 (m, 4H), 3.819 (s, 6H), 3.389 (dd, J=13.8, 3.72 Hz, 1H), 2.827 (m, 1H). MS (ESI) m/z 585 (M$^+$+H).

Example 4

Synthesis of Compound 631

Synthesis of N-(4-(3-(1H-1,2,4-triazol-1-yl)-4-(3,4,5-trimethoxybenzoyl)phenyl) thiazol-2-yl)-2-(dimethylamino)acetamide N,N-dimethylglycine (446.8 mg, 4.33 mmol) and N,N-dimethylformamide (one drop) were dissolved in methylene chloride (5 mL), thionyl chloride (SOCl$_2$, 0.41 mL) was added thereto at ambient temperature and the resulting mixture was stirred at 70° C. for one hour. After the reaction was completed, the reaction solution was cooled to ambient temperature and dried under reduced pressure to remove the solvent to obtain a compound 5 as an intermediate. The compound 516 (94.6 mg, 0.22 mmol) was dissolved in methylene chloride (5 mL) and pyridine (26.2 µL), the compound 5 (68.3 mg) was added thereto and the resulting mixture was stirred at ambient temperature overnight. After the reaction was completed, the reaction solution was dried under reduced pressure to remove the solvent and the resulting product was purified by column chromatography (SiO$_2$, MC/MeOH 40/1-5/1) to obtain a brown compound 631 (24.1 mg, 21.3%).

$^1$H NMR (400 MHz, acetone) δ 8.760 (s, 1H), 8.302 (d, J=1.28 Hz, 1H), 8.231 (dd, J=8.0, 1.6 Hz, 1H), 7.871 (s, 2H), 7.718 (d, J=8.12 Hz, 1H), 6.995 (s, 2H), 3.796 (s, 6H), 3.785 (s, 3H), 3.000 (s, 2H), 2.430 (s, 6H). MS (ESI) m/z 523 (M$^+$+H).

Example 5

Synthesis of Compound 646

Synthesis of (S)—N-(4-(3-(1H-1,2,4-triazol-1-yl)-4-(3,4,5-trimethoxybenzoyl)phenyl)thiazol-2-yl)pyrrolidine-2-carboxamide A white solid compound 646 (7.8 mg, 25.1%) was obtained in the same manner as in the synthesis of the compound 615.

$^1$H NMR (400 MHz, MeOD) δ 8.817 (s, 1H), 8.268 (m, 2H), 7.940 (s, 1H), 7.845 (s, 1H), 7.744 (m, 1H), 6.970 (s, 2H), 4.068-4.037 (m, 1H), 3.826 (s, 3H), 3.789 (s, 6H), 3.181 (m, 1H), 2.686-2.617 (m, 1H), 2.344-2.263 (m, 1H), 2.344 (m, 1H), 2.005-1.841 (m, 3H). MS (ESI) m/z 535 (M$^+$+H).

Example 6

Synthesis of Compound 647

Synthesis of (S)—N-(4-(3-(1H-1,2,4-triazol-1-yl)-4-(3,4,5-trimethoxybenzoyl)phenyl)thiazol-2-yl)-2-amino-4-methylpentanamide A white solid compound 647 (8.5 mg, 23.6%) was obtained in the same manner as in the synthesis of the compound 615.

$^1$H NMR (400 MHz, CDCl$_3$) δ 8.311 (s, 1H), 8.105-8.055 (m, 2H), 7.942 (s, 1H), 7.649 (d, J=7.96 Hz, 1H), 7.439 (s, 1H), 6.978 (s, 2H), 3.892 (s, 3H), 3.814 (s, 6H), 3.742-3.725 (m, 1H), 1.999-1.925 (m, 2H), 1.508-1.462 (m, 1H), 1.018 (t, J=5.96 Hz, 6H). MS (ESI) m/z 551 (M$^+$+H).

Example 7

Synthesis of Compound 648

Synthesis of (S)—N-(4-(3-(1H-1,2,4-triazol-1-yl)-4-(3,4,5-trimethoxybenzoyl) phenyl)thiazol-2-yl)-2-amino-3-cyclohexylpropane amide A white solid compound 648 (46.8 mg, 36%) was obtained in the same manner as in the synthesis of the compound 615.

$^1$H NMR (400 MHz, CDCl$_3$) δ 8.305 (s, 1H), 8.099-8.049 (m, 2H), 7.936 (s, 1H), 7.643 (d, J=8.04 Hz, 1H), 7.434 (s, 1H), 7.257 (s, 1H), 6.972 (s, 2H), 3.886 (s, 3H), 3.783-3.748 (m, 7H), 2.044-1.309 (m, 13H). MS (ESI) m/z 631 (M$^+$+40).

Example 8

Synthesis of Compound 652

Synthesis of N-(4-(3-(1H-1,2,4-triazol-1-yl)-4-(3,4,5-trimethoxybenzoyl)phenyl) thiazol-2-yl)-2-amino-3-methylbutanamide A white solid compound 652 (258.2 mg, 63.1%) was obtained using Fmoc-valine (racemic isomer) in the same manner as in the synthesis of the compound 615.

1H NMR (400 MHz, CDCl$_3$) δ 8.338 (s, 1H), 8.172 (d, J=1.52 Hz, 1H), 8.035 (dd, J=8.08, 1.40 Hz, 1H), 7.937 (s, 1H), 7.653 (d, J=8.08 Hz, 1H), 7.381 (s, 1H), 6.985 (s, 2H), 3.819 (s, 6H), 3.556 (d, J=3.6 Hz, 1H), 2.481 (m, 1H), 1.092 (d, J=6.96 Hz, 3H), 0.909 (d, J=6.92 Hz, 3H). MS (ESI) m/z 537 (M$^+$+H).

Example 9

Synthesis of Compound 653

Synthesis of (R)—N-(4-(3-(1H-1,2,4-triazol-1-yl)-4-(3,4,5-trimethoxybenzoyl) phenyl)thiazol-2-yl)-2-amino-3-methylbutanamide A white solid compound 653 (2.25 g, 53.2%) was obtained using Fmoc-D-valine in the same manner as in the synthesis of the compound 615.

$^1$H NMR (400 MHz, CDCl$_3$) δ 8.338 (s, 1H), 8.172 (d, J=1.52 Hz, 1H), 8.035 (dd, J=8.08, 1.40 Hz, 1H), 7.937 (s, 1H), 7.653 (d, J=8.08 Hz, 1H), 7.381 (s, 1H), 6.985 (s, 2H), 3.819 (s, 6H), 3.556 (d, J=3.6 Hz, 1H), 2.481 (m, 1H), 1.092 (d, J=6.96 Hz, 3H), 0.909 (d, J=6.92 Hz, 3H). MS (ESI) m/z 537 (M$^+$+H).

Experimental Example 1

Measurement of Solubility in Water

The compounds of the present invention were developed to reduce toxicity caused by deposition on organ due to low solubility of compound 516, as confirmed by animal tests. Considering this, solubility of the present compounds in water was thus measured.

(1) Test Methods
Determination of Calibration Line
The compound was dissolved in acetonitrile to a concentration of 1 mg/mL and the solution was diluted with a mobile phase to a concentration of 5, 12.5, 25, 50 or 100 μg/ml.
Preparation of Specimen
1. The compound was added to distilled water such that the concentration of each specimen was adjusted to 10 mg/mL, stirred in a thermostat stirrer (25° C., 200 rpm) for about 7 days, filtered and diluted with a mobile phase to an optimal concentration.
2. The compound was added to distilled water such that the concentration of each specimen was adjusted to 10 mg/mL, sonicated for 30 minutes, stirred for 5 minutes, filtered, sonicated for 30 minutes again and diluted with a mobile phase to an optimal concentration.
(2) HPLC Conditions
UV: 215 nm
Flow rate: 1 mL/mL
Amount injected: 10 μl
Column temperature: 25° C.
Column: Kromasil C8 (4.6×150 mm, 5 μm)
Mobile phase: 20 mM ammonium acetate, pH 5.0/ACN (60/40)
(3) Test Results
The solubility of the compounds of the present invention was compared with that of the compound 516 and the results thus obtained are shown in Table 2 below.

compounds of the present invention exhibited high solubility of 10 mg/mL or higher, which are comparable to or higher than a currently available reference drug, AC7700 (See: Anticancer Drug Des. 1999, December; 14(6): 539-48).

Experimental Example 2

Pharmaceutical Effects of the Compound in Mice (1) Test Animal
BALB/c male nude mice (4 weeks) available from Central Lab Animal Inc. were used for human xenograft experiments. Sterile food and potable water were freely provided to the mice in an isolated sterile cage and the temperature of the cage was maintained at 23±0.5° C.
(2) Cell Lines
A human cancer model, CX-1 (human colon adenocarcinoma), for xenograft experiment was obtained from the German Cancer Research Center (DKFZ), and HCT-15 (human colorectal adenocarcinoma, CCL-225) and A549 (human lung carcinoma, CCL-185) were obtained from ATCC (American Type Culture Collection, Rockville, Md., USA). Human tumor cells, MKN45 (human gastric adenocarcinoma, #80103) and calu-6 (human lung carcinoma, #30056) were obtained from KCLB (Korean Cell Line. Bank).
CX-1 was incubated in a 95% air incubator (37° C., 5% CO$_2$) using a DMEM (Dulbecco's Modified Eagle's Medium, Gibco) supplemented with 10% heat-inactivated fetal bovine serum (Gibco) and 1% Antibiotics-Antimycotics (Gibco). Other cell lines were incubated in a 95% air incubator (37° C., 5% CO$_2$) using an RPM1640 (Gibco BRL) medium supplemented with 10% heat-inactivated fetal bovine serum (Gibco) and 1% Antibiotics-Antimycotics (Gibco).
(3) In Vivo Antitumor Activity
In vivo human xenograft experiments were performed in accordance with the following procedure. In vitro proliferated human-derived cancer cell lines (CX-1, HCT-15, A549, MKN45, calu-6) were subcutaneously injected into the abdominal region of BALB/c nude mice and were thus proliferated in vivo. After 20 to 25 days, the mice were sacrificed by cervical spine dislocation, solid cancer cells proliferated in the mice were sterilely separated and fresh cancer cells from which connective or necrotic tissues or skin were removed were collected. The fragments of tumor were transplanted to the BALB/c nude mice.
The mice in which cancer cells were proliferated to a predetermined size were collected on the 15$^{th}$ to 30$^{th}$ day after human-derived cancer models were transplanted into the BALB/c nude mice and then used for the tests. For each experimental group, the drug was injected at a dose of 0.1 mL per 10 g of mouse in accordance with a dose schedule, when tumor cells were grown to a size of 100 to 200 mm$^3$ after tumor transplantation.
After administration, antitumor activity was evaluated based upon an antitumor inhibition rate (IR %) of tumor

TABLE 2

|  | Compound 516 | Compound 615 | Compound 624 | Compound 625 | Compound 631 | Compound 646 | Compound 647 | Compound 648 |
| --- | --- | --- | --- | --- | --- | --- | --- | --- |
| Solubility (mg/mL) | 0.5 | 23.3 | 14.9 | 11.0 | 25.4 | 29.1 | 12.1 | 12.5 |

As can be seen from Table 2 above, the compound 516 exhibited considerably low solubility of 0.5 mg/mL, while the growth, obtained by comparing a tumor volume measured on the final day with a tumor volume of a control group. As the reference drug, AC7700 (Sanofi-Aventis), which is currently undergoing phase III clinical trials, was used.

Tumor size=(short diameter)$^2$×(long diameter)/2

I.R.(%)=[1−(average tumor size of drug-administered group)/(average tumor size of control group)]× 100

The results of pharmaceutical effect tests of the compound 516 using human-derived colorectal cancer model (CX-1) are shown in Table 3 below and FIG. 1. FIG. 1 is a graph showing tumor volume on each administration day of compound 516.

TABLE 3

| Experimental group (n = 6) | Dose/day | Administration method | Body weight change (%) | IR (%) | Number of dead animals |
|---|---|---|---|---|---|
| Control group | — | — | +18.4 | — | 0/6 |
| AC7700 | 100 mg/kg | q4d x 4 (i.p.) | +13.2 | 48% | 2/6 |
| Compound 516 | 5 mg/kg | q4d x 4 (i.p.) | +15.2 | 36% | 2/6 |

As can be seen from Table 3 above and FIG. 1, in the results of CX-1 xenograft model, the compound 516 exhibited significantly superior pharmaceutical effects, as compared to the reference drug, AC7700, but two animals died on the 6$^{th}$ and 7$^{th}$ day due to strong toxicity in vivo, which indicates that the compound 516 has a considerably narrow safety margin.

Figure 2:
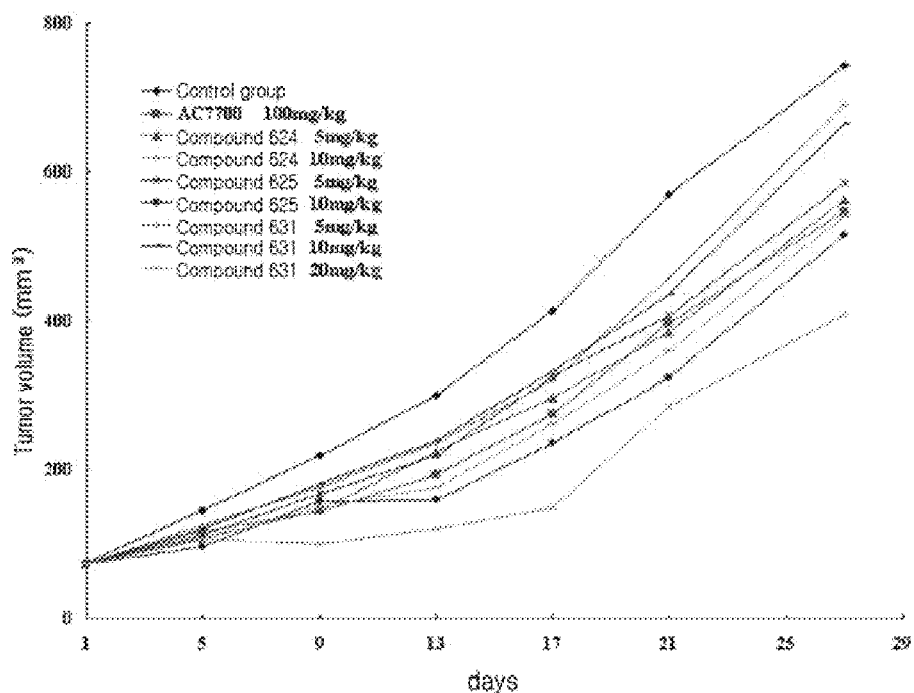
FIG. 2 is a graph showing tumor volume on each administration day of compounds 624, 625 and 631, as a result of pharmaceutical effect tests of the compounds using a human-derived colorectal cancer cell line (CX-1)

The results of pharmaceutical effect tests of the compounds 624, 625 and 631 using human-derived colorectal cancer model (CX-1) are shown in Table 4 below and FIG. 2. FIG. 2 is a graph showing tumor volume on each administration day of compounds 624, 625 and 631.

TABLE 4

| Experimental group (n = 6) | Dose/day | Administration method | Body weight change (%) | IR (%) | Number of dead animals |
|---|---|---|---|---|---|
| Control group | — | — | +24.5 | — | 0/6 |
| AC7700 | 100 mg/kg | q4d x 4 (i.p.) | +22.8 | 34% | 0/6 |
| Compound 624 | 5 mg/kg | q4d x 4 (i.p.) | +25.7 | 28% | 0/6 |
|  | 10 mg/kg |  | +14.7 | 64% |  |
| Compound 625 | 5 mg/kg | q4d x 4 (i.p.) | +28.9 | 21% | 0/6 |
|  | 10 mg/kg |  | +24.5 | 43% |  |
| Compound 631 | 5 mg/kg | q4d x 4 (i.p.) | +24.8 | 23% | 0/6 |
|  | 10 mg/kg |  | +26.7 | 20% |  |
|  | 20 mg/kg |  | +20.9 | 37% |  |

As can be seen from Table 4 above and FIG. 2, in the result of CX-1 xenograft model, the compounds 624, 625 and 631 exhibited significantly superior pharmaceutical effects, as compared to the reference drug, AC7700, underwent no weight loss, as compared to the compound 516, and caused no animal death, which indicates that the compounds have considerably improved safety. In particular, the compound 624 exhibited double the pharmaceutical effects of the reference drug.

Figure 3:
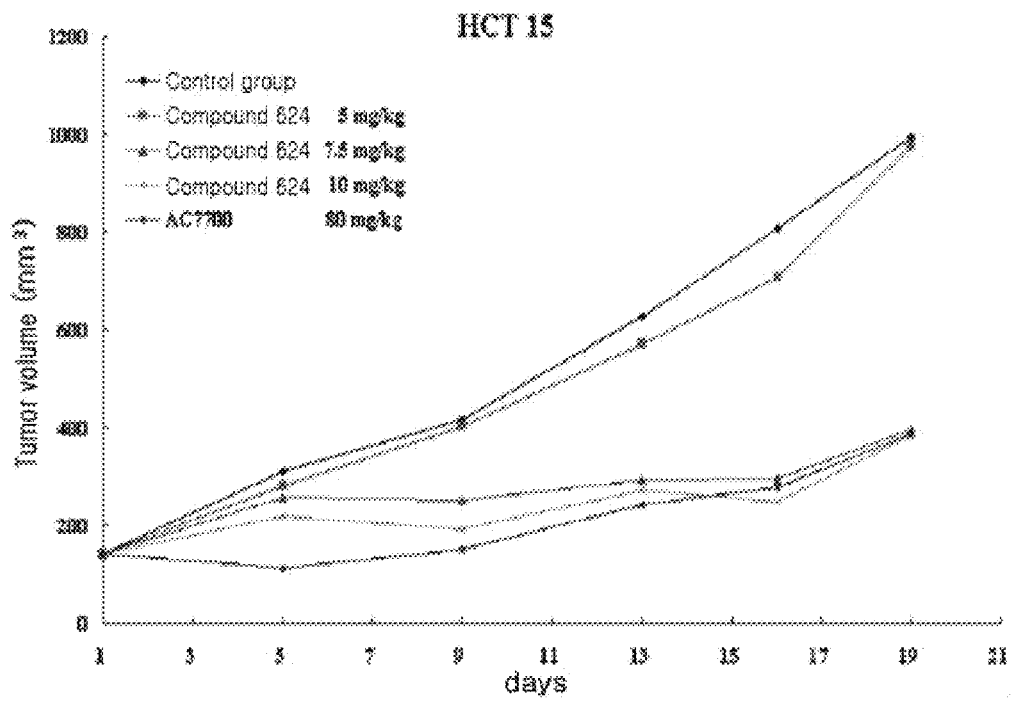
FIG. 3 is a graph showing tumor volume on each administration day of compound 624, as a result of pharmaceutical effect tests of the compound 624 using a human-derived colorectal cancer cell line (HCT-15)

③ The results of pharmaceutical effect tests of the compound 624 using human-derived colorectal cancer model (HCT-15) are shown in Table 5 below and FIG. 3. FIG. 3 is a graph showing tumor volume on each administration day of compound 624.

TABLE 5

| Experimental group (n = 6) | Dose/day | Administration method | Body weight change (%) | IR (%) | Number of dead animals |
|---|---|---|---|---|---|
| Control group | — | — | −3.4 | — | 0/6 |
| AC7700 | 80 mg/kg | q4d x 4 (i.p.) | +5.5 | 66% | 1/6 |
| Compound 624 | 5 mg/kg | q4d x 4 (i.p.) | +1.8 | 12% | 0/6 |
|  | 7.5 mg/kg |  | +3.2 | 63% | 0/6 |
|  | 10 mg/kg |  | +6.6 | 69% | 0/6 |

As can be seen from Table 5 above and FIG. 3, in the result of additional HCT-15 xenograft model, the compound 624 also exhibited significantly superior pharmaceutical effects, as compared with the reference drug.

Figure 4:
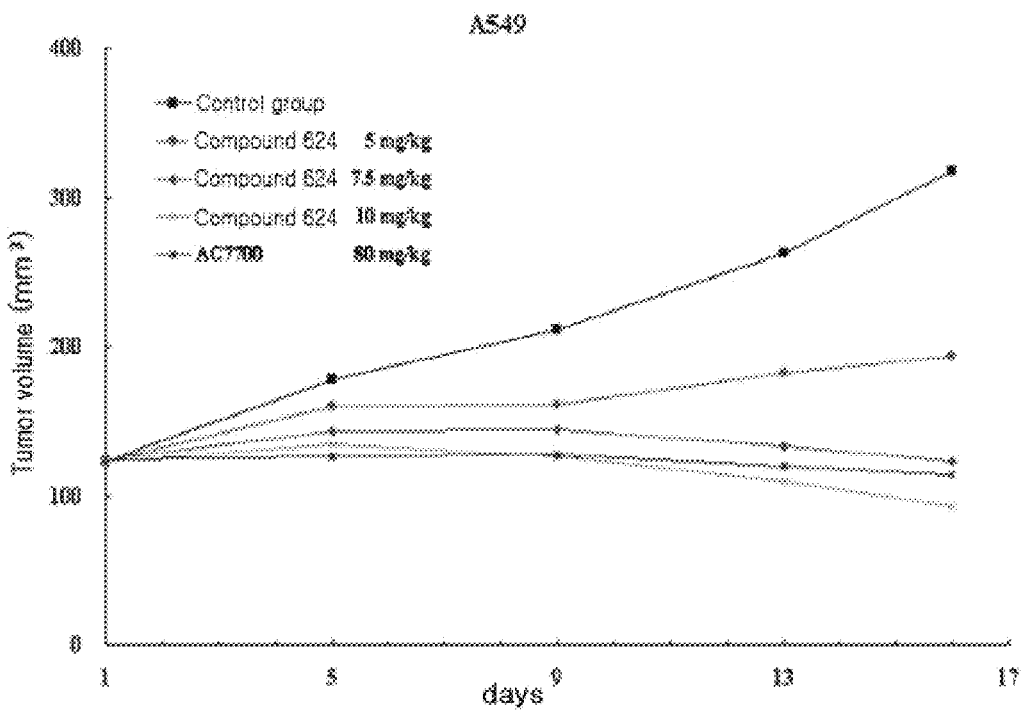
FIG. 4 is a graph showing tumor volume on each administration day of compound 624, as a result of pharmaceutical effect tests of the compound 624 using a human-derived lung cancer cell line (A549)

The results of pharmaceutical effect tests of the compound 624 using human-derived lung cancer model (A549) are shown in Table 6 below and FIG. 4. FIG. 4 is a graph showing tumor volume on each administration day of compound 624.

TABLE 6

| Experimental group (n = 7) | Dose/day | Administration method | Body weight change (%) | IR (%) | Number of dead animals |
|---|---|---|---|---|---|
| Control group | — | — | +5.4 | — | 0/7 |
| AC7700 | 80 mg/kg | q4d x 4 (i.p.) | +2.6 | 64% | 0/7 |
| Compound 624 | 5 mg/kg | q4d x 4 (i.p.) | −1.7 | 39% | 0/7 |
|  | 7.5 mg/kg |  | +1.7 | 61% | 0/7 |
|  | 10 mg/kg |  | −1.2 | 71% | 0/7 |

As can be seen from Table 6 above and FIG. 4, in the result of additional A549 xenograft model, the compound 624 also exhibited significantly superior pharmaceutical effects, as compared with the reference drug.

Figure 5:
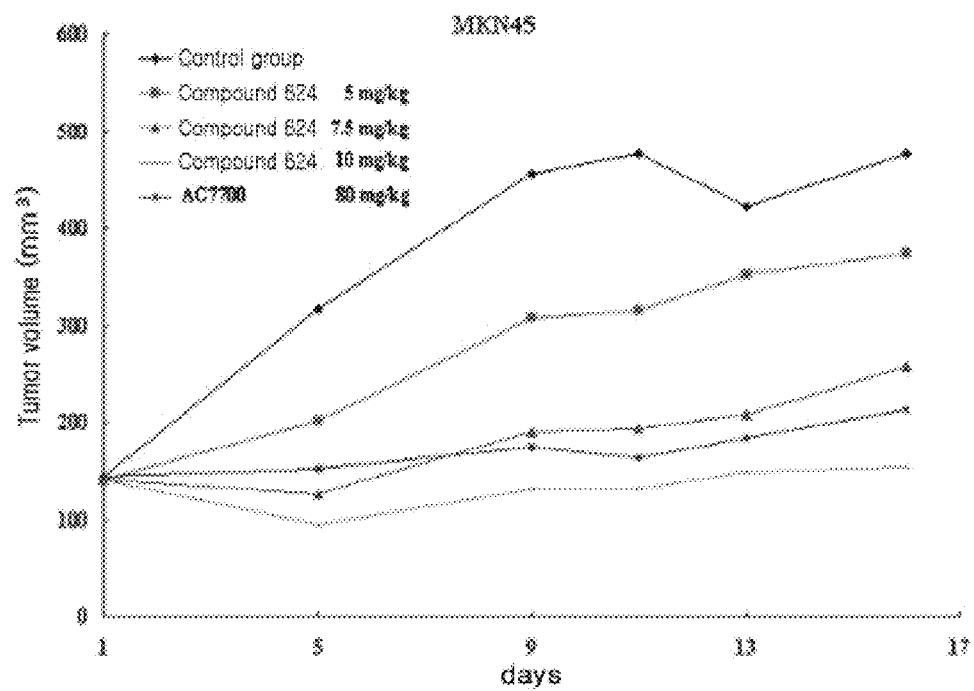
FIG. 5 is a graph showing tumor volume on each administration day of compound 624, as a result of pharmaceutical effect tests of the compound 624 using a human-derived stomach cancer cell line (MKN45)

The results of pharmaceutical effect tests of the compound 624 using human-derived stomach cancer model (MKN45) are shown in Table 7 below and FIG. 5. FIG. 5 is a graph showing tumor volume on each administration day of compound 624.

TABLE 7

| Experimental group (n = 6) | Dose/day | Administration method | Body weight change (%) | IR (%) | Number of dead animals |
|---|---|---|---|---|---|
| Control group | — | — | −15.3 | — | 0/6 |
| AC7700 | 80 mg/kg | q4d x 4 (i.p.) | +7.8 | 55% | 0/6 |
| Compound 624 | 5 mg/kg | q4d x 4 (i.p.) | −11.8 | 21% | 0/6 |
|  | 7.5 mg/kg |  | +2.9 | 46% | 0/6 |
|  | 10 mg/kg |  | +4.3 | 68% | 0/6 |

As can be seen from Table 7 above and FIG. 5, in the result of additional MKN45 xenograft model, the compound 624 also exhibited significantly superior pharmaceutical effects, as compared with the reference drug.

Figure 6:
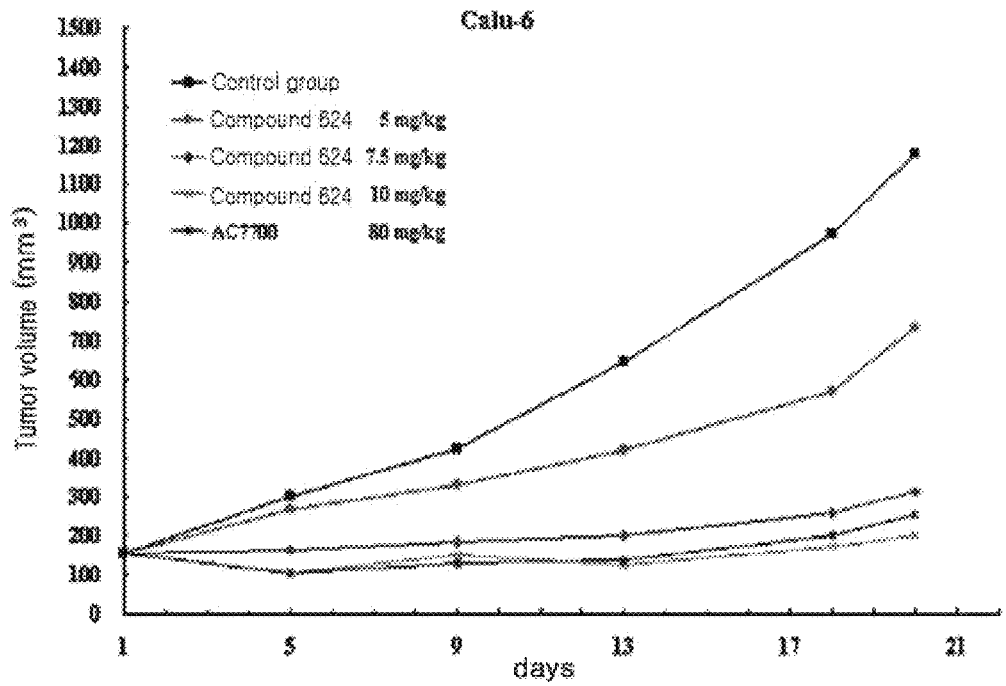
FIG. 6 is a graph showing tumor volume on each administration day of compound 624, as a result of pharmaceutical effect tests of the compound 624 using a human-derived non-small cell lung cancer cell line (calu-6).

The results of pharmaceutical effect tests of the compound 624 using human-derived non-small cell lung cancer model (calu-6) are shown in Table 8 below and FIG. 6. FIG. 6 is a graph showing tumor volume on each administration day of compound 624.

TABLE 8

| Experimental group (n = 6) | Dose/day | Administration method | Body weight change (%) | IR (%) | Number of dead animals |
|---|---|---|---|---|---|
| Control group | — | — | +30.0 | — | 0/6 |
| AC7700 | 80 mg/kg | q4d x 4 (i.p.) | +22.4 | 80% | 0/6 |
| Compound 624 | 5 mg/kg | q4d x 4 (i.p.) | +26.2 | 41% | 0/6 |
|  | 7.5 mg/kg |  | +26.0 | 73% | 0/6 |
|  | 10 mg/kg |  | +20.6 | 82% | 0/6 |

As can be seen from Table 8 above and FIG. 6, in the result of additional calu-6 xenograft model, the compound 624 also exhibited significantly superior pharmaceutical effects, as compared with the reference drug.

INDUSTRIAL APPLICABILITY

As apparent from the fore-going, the benzophenone thiazole derivative of the present invention inhibits formation of microtubules and eliminates actively proliferating cells of malignant tumors, thus being useful as therapeutic agents for malignant tumors, viral and bacterial infection, recurrent vascular occlusion, inflammatory diseases, autoimmune diseases and psoriasis.

The invention claimed is:
1. A compound represented by formula (1) below or a stereoisomer thereof, and a pharmaceutically acceptable salt thereof:

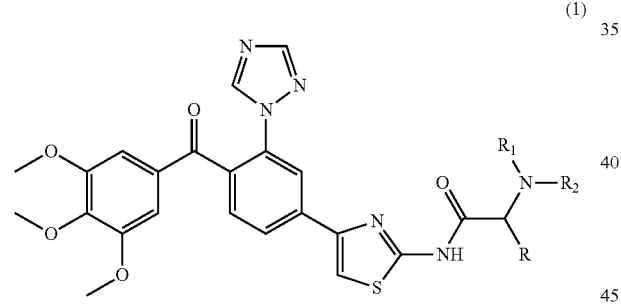

(1)

wherein
$R_1$ and $R_2$ are each independently hydrogen or methyl; and
R is joined with $R_1$ or $R_2$ to form a 5-membered ring or R is selected from the group consisting of hydrogen, methyl, ethyl,

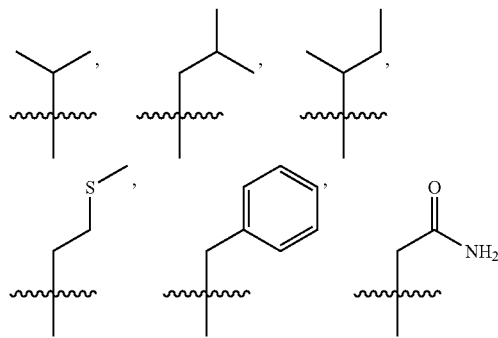

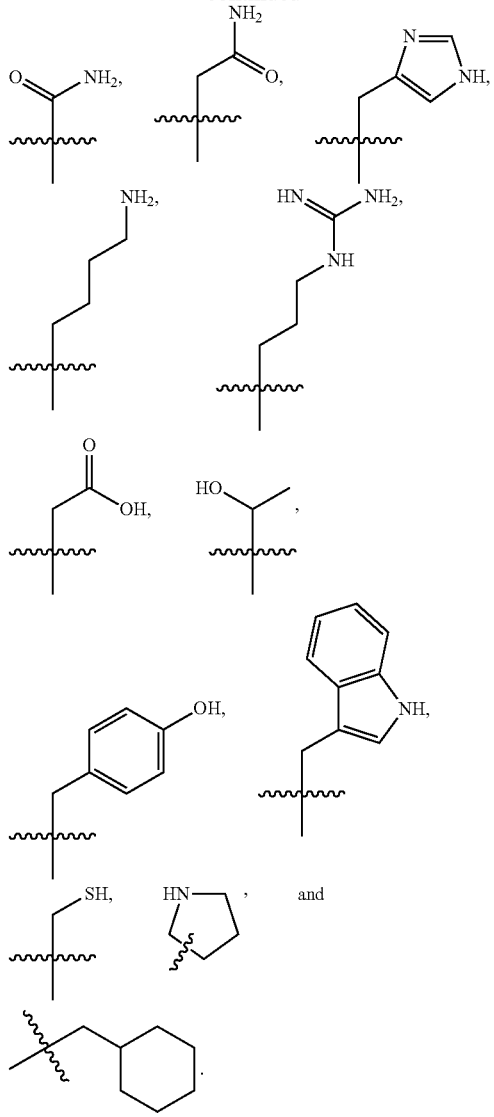

2. The compound according to claim 1 selected from the group consisting of:
N-(4-(3-(1H-1,2,4-triazol-1-yl)-4-(3,4,5-trimethoxybenzoyl)phenyl)thiazol-2-yl)-2-aminoacetamide;
(S)—N-(4-(3-(1H-1,2,4-triazol-1-yl)-4-(3,4,5-trimethoxybenzoyl)phenyl)thiazol-2-yl)-2-amino-3-methylbutanamide;
(S)—N-(4-(3-(1H-1,2,4-triazol-1-yl)-4-(3,4,5-trimethoxybenzoyl)phenyl)thiazol-2-yl)-2-amino-3-phenylpropanamide;
N-(4-(3-(1H-1,2,4-triazol-1-yl)-4-(3,4,5-trimethoxybenzoyl)phenyl)thiazol-2-yl)-2-(dimethylamino)acetamide;
(S)—N-(4-(3-(1H-1,2,4-triazol-1-yl)-4-(3,4,5-trimethoxybenzoyl)phenyl)thiazol-2-yl)pyrolidine-2-carboxamide;
(S)—N-(4-(3-(1H-1,2,4-triazol-1-yl)-4-(3,4,5-trimethoxybenzoyl)phenyl)thiazol-2-yl)-2-amino-4-methylpentanamide;
(S)—N-(4-(3-(1H-1,2,4-triazol-1-yl)-4-(3,4,5-trimethoxybenzoyl)phenyl)thiazol-2-yl)-2-amino-3-cyclohexylpropanamide;

N-(4-(3-(1H-1,2,4-triazol-1-yl)-4-(3,4,5-trimethoxybenzoyl)phenyl)thiazol-2-yl)-2-amino-3-methylbutanamide; and (R)—N-(4-(3-(1H-1,2,4-triazol-1-yl)-4-(3,4,5-trimethoxybenzoyl)phenyl)thiazol-2-yl)-2-amino-3-methylbutanamide.

3. The compound according to claim 1, wherein the compound is (S)—N-(4-(3-(1H-1,2,4-triazol-1-yl)-4-(3,4,5-trimethoxybenzoyl)phenyl)thiazol-2-yl)-2-amino-3-methylbutanamide.

4. The compound according to claim 1, wherein the compound is (S)—N-(4-(3-(1H-1,2,4-triazol-1-yl)-4-(3,4,5-trimethoxybenzoyl)phenyl)thiazol-2-yl)-2-amino-3-phenylpropanamide.

5. A pharmaceutical composition, comprising the compound according to claim 1 as an active ingredient, and a pharmaceutically acceptable excipient or carrier.

6. A method for preparing a compound represented by formula (6), comprising reacting a (Compound 516), [{4-(2-aminothiazol-4-yl)-2-(1H-1,2,4-triazol-1-yl)phenyl}(3,4,5-trimethoxyphenyl)methanone], with a compound represented by formula (3) or formula (5):

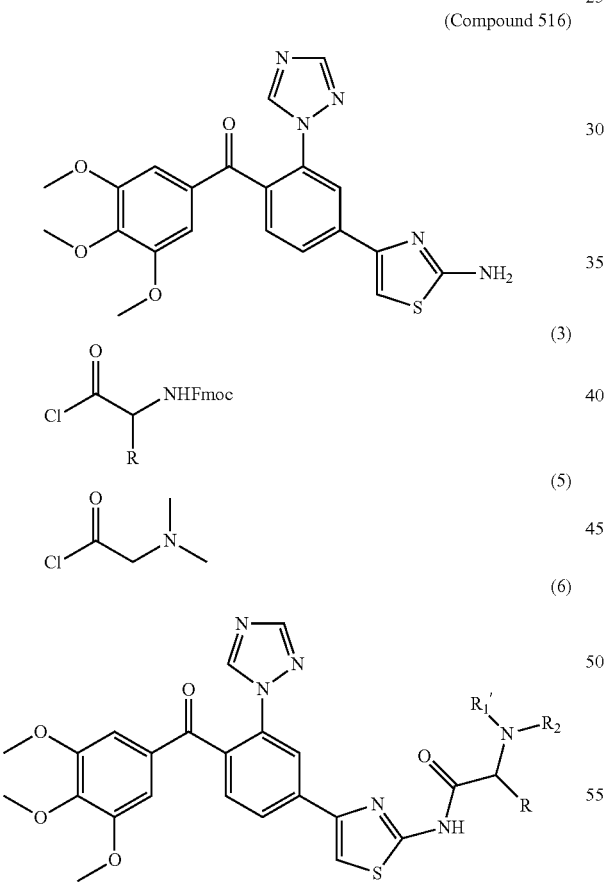

wherein $R_1'$ is Fmoc(9-fluorenylmethoxycarbonyl) group or $CH_3$; $R_2$ is H or $CH_3$; and R is joined with $R_2$ to form a 5-membered ring or R is selected from the group consisting of hydrogen, methyl, ethyl,

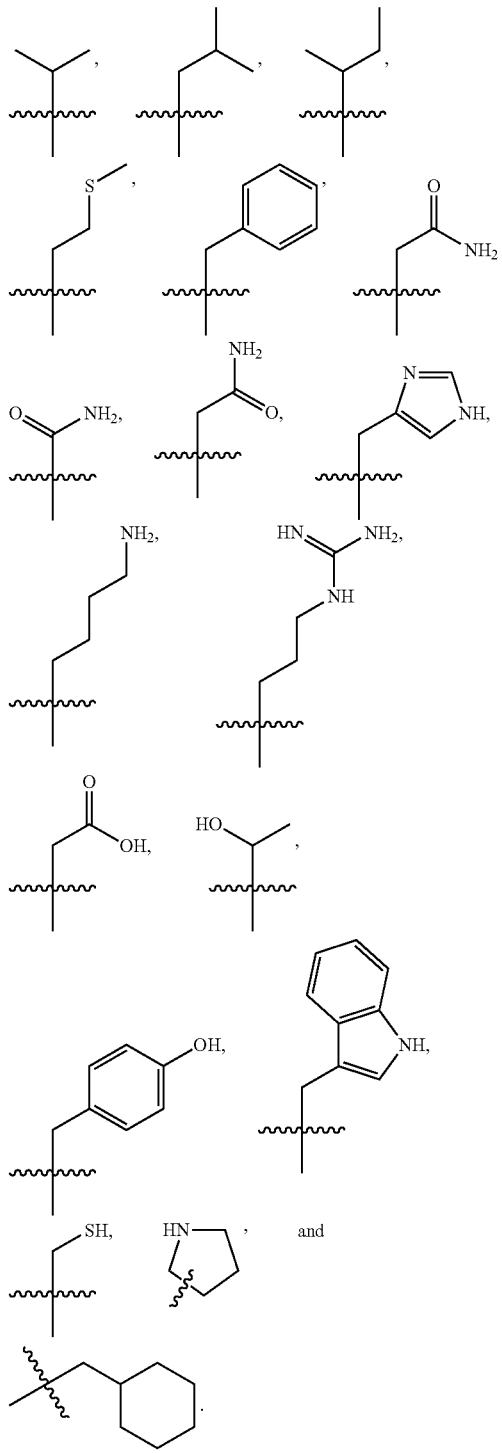

* * * * *

UNITED STATES PATENT AND TRADEMARK OFFICE
CERTIFICATE OF CORRECTION

PATENT NO. : 8,362,267 B2
APPLICATION NO. : 12/934521
DATED : January 29, 2013
INVENTOR(S) : Choi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
First Day of September, 2015

Michelle K. Lee
*Director of the United States Patent and Trademark Office*